(12) United States Patent
Doyle

(10) Patent No.: US 6,224,547 B1
(45) Date of Patent: May 1, 2001

(54) TONGUE DEPRESSOR FOR USE ON ORAL EXAMINATIONS

(76) Inventor: Donald E. Doyle, 4105 Hospital Rd., Suite 102-A, Pascagoula, MS (US) 39581

( * ) Notice: Subject to any disclaimer, the term of this patent is extended or adjusted under 35 U.S.C. 154(b) by 0 days.

(21) Appl. No.: 09/449,397

(22) Filed: Nov. 26, 1999

Related U.S. Application Data

(60) Provisional application No. 60/110,887, filed on Dec. 4, 1998.

(51) Int. Cl.[7] ........................................ A61B 1/32
(52) U.S. Cl. ........................................ 600/240; 600/210
(58) Field of Search .................... 600/184, 201, 600/210, 235, 237, 240, 241, 185, 190, 193, 195, 191, 186, 194, 197, 203, 206, 213, 226, 239, 242

(56) References Cited

U.S. PATENT DOCUMENTS

| | | |
|---|---|---|
| 2,723,661 * | 11/1955 | Hull . |
| 3,397,687 * | 8/1968 | Kirchdoerfer . |
| 5,518,503 * | 5/1996 | Rooney et al. ................ 600/240 |
| 6,045,499 * | 4/2000 | Pitesky ................ 600/240 |

FOREIGN PATENT DOCUMENTS

| | | | |
|---|---|---|---|
| 966030 * | 4/1975 | (CA) | ................ 600/240 |
| 494840 * | 7/1992 | (EP) | ................ 600/240 |

OTHER PUBLICATIONS

Item No. 20, John Reynders & Co. (Catalog), New York, p. 233, 1895.*

* cited by examiner

Primary Examiner—Jeffrey A. Smith
(74) Attorney, Agent, or Firm—Roger A. Marrs

(57) ABSTRACT

A tongue depressor, including an elongated strip or body having opposite ends separated by a flat midsection wherein each end is curved in an opposite or reverse direction. One end of the strip is curved upwardly while the opposite end of the strip is curved downwardly. The entire length of the strip may embody a slight, weak, or shallow curve. The width of the strip may be wider than commonly employed and also, the respective opposite ends of the strip may be wider than the midsection which interconnects the opposite ends. A separate end section may include a doubled over depressor piece and the section may insertably receive the end of a flat stick.

7 Claims, 1 Drawing Sheet

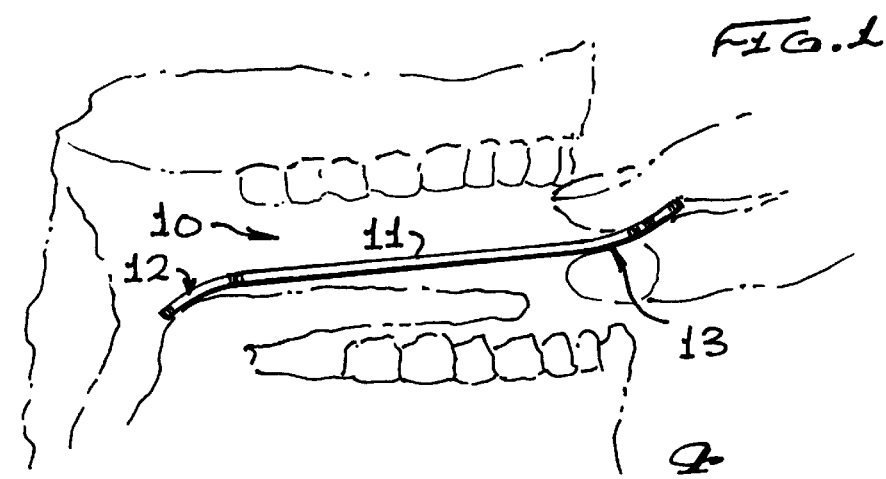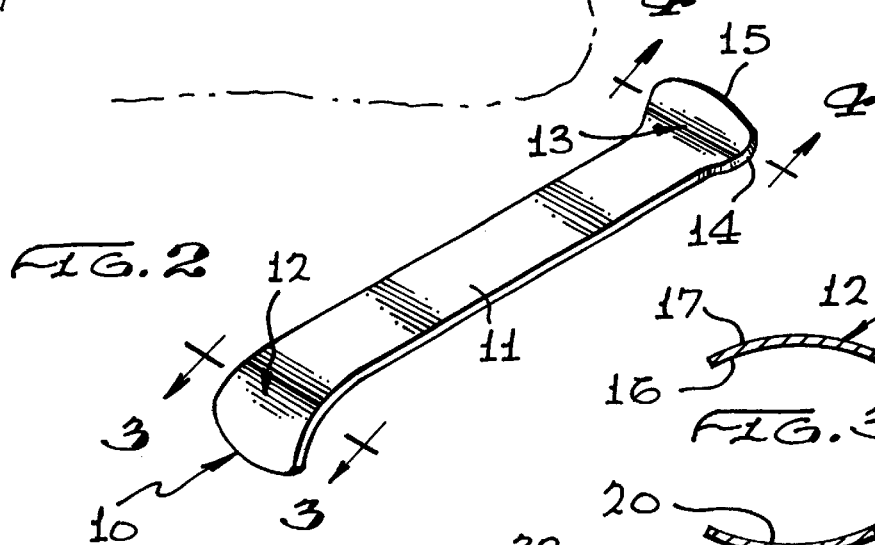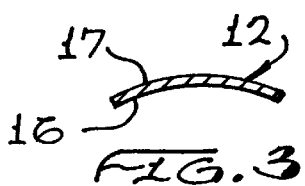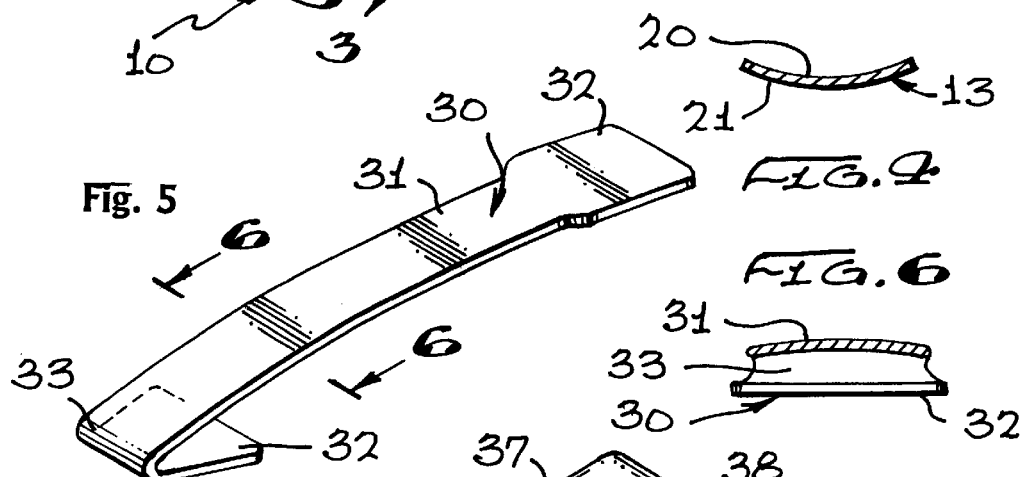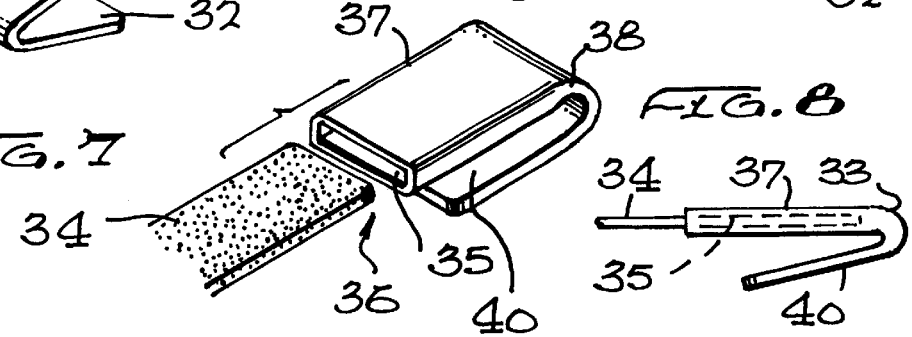

ered over a wide area with an entire section of the tongue rather than just the central 25% to 30% of the tongue area which a standard or conventional flat tongue blade does.

TONGUE DEPRESSOR FOR USE ON ORAL EXAMINATIONS

Priority based on Ser. No. 60/110,887 filed Dec. 4, 1998.

BACKGROUND OF THE INVENTION

1. Field of the Invention

The present invention relates to the field of hygienic tongue depressors, and more particularly to a novel tongue depressor that is curved at least at one end so that the base of the tongue during use is depressed allowing the health care provider to visually observe the epiglottis.

2. Brief Description of the Prior Art

In the past, tongue depressors have been employed to hold and retain the tongue or a patient's lips out of the line of vision during inspections of the mouth. The conventional tongue depressor includes a stick with a flat length and is rounded at its ends. However, there are frequent occasions in which a satisfactory inspection of the mouth cannot be made because the view of the interior of the mouth and throat is obstructed after the tongue or the lips have been depressed or moved as far as possible. Furthermore, the conventional or standard tongue depressor of the blade type does not address a wide tongue which does not yield readily so that the result is a mounding of glossal tissue around the sides or edges of the blade itself. Also, conventional tongue depressors do not provide proper or adequate visualization of the anatomical structure known as the epiglottis. The epiglottis is usually below the level of the tongue posterior overlying the laryngeal inlet. This is an important structure to observe, especially in children who not uncommonly have inflammation and infection of this anatomical structure.

Still a further problem with conventional depressors resides in performing an indirect laryngoscopy requiring visualization of the larynx with a mirror. Usually, the physician holds the anterior portion of the tongue by the tip usually with a gauze sponge and then uses the fingers of his other hand to work the mirror. Sometimes the patient involuntarily, while not gagging, will have his tongue elevated when he is repeating the vocal command "EEEE" making proper visualization impossible. During this procedure, physicians sometimes take the tongue blade of conventional design and place it between the second and third fingers of his left hand while the first and second digits are holding the tongue. Then, with only the strength of his middle finger, the physician attempts to use the tongue depressor or blade to depress the offending tissue. Such a procedure is tedious and requires substantial dexterity.

Therefore, a long-standing need has existed to provide a tongue depressor which can do both of the above-mentioned hand functions and which is convenient to grasp the tip of the tongue while simultaneously depressing the posterior aspect of the tongue with one pincers movement. Also, it would be helpful to shape the depressor in such a way as to depress the base of the tongue while allowing for observation of the epiglottis.

SUMMARY OF THE INVENTION

The above problems and difficulties have been avoided by the present invention which provides a novel tongue depressor, including an elongated strip having opposite ends separated by a flat midsection wherein each end is curved in a reverse or opposite direction. For example, one end of the strip is curved upwardly while the opposite end of the strip is reversed to curve downwardly. In some instances, only one end of the strip is curved and in other instances, the entire length of the strip may embody a slight or weak curve from one end to the other. Preferably, the width of the strip is wider than commonly employed and also, the respective opposite ends of the strip are wider than the midsection which interconnects the opposite ends. Also, the curved ends may be separate components having a receptacle to insertably receive a flat end of the depressor midsection.

Therefore, it is among the primary objects of the present invention to provide a tongue depressor which allows the health care provider to grasp and control the tongue anteriorly and which maintains control of the tongue posterior at the same time so that the health care provider is permitted to lift the tongue and observe the floor of the mouth and the underside of the tongue.

Another object of the present invention is to provide a novel type of depressor which allows the user to manipulate the tongue from one side to the other in order to observe the length of the tongue on the left and the right sides and which allows visualization of the epiglottis.

A further object resides in a tongue depressor which depresses a large portion of the tongue rather than just the central 25% to 30% of the tongue area which a standard or conventional flat tongue blade does.

A further object resides in providing a novel tongue depressor which allows observation of the larynx with a mirror for indirect laryngoscopy.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a side elevational view of the novel tongue depressor incorporating the present invention illustrated in connection with depressing the tongue of a patient;

FIG. 2 is a front perspective view of the tongue depressor shown in FIG. 1;

FIG. 3 is a transverse cross-sectional view of the tongue depressor shown in FIG. 2 as taken in the direction of arrows 3—3 thereof;

FIG. 4 is a transverse cross-sectional view of the tongue depressor as taken in the direction of arrows 4—4 of FIG. 2;

FIG. 5 is a front perspective view of another version of a tongue depressor having rounded ends incorporating the present invention;

FIG. 6 is a transverse cross-sectional view of the tongue depressor shown in FIG. 5 as taken in the direction of arrows 6—6 thereof;

FIG. 7 is an exploded perspective view showing another version of a curve ended tongue depressor incorporating the present invention; and FIG. 8 is a fragmentary side elevational view of the curve ended tongue depressor shown in FIG. 7.

DESCRIPTION OF THE PREFERRED EMBODIMENTS

Referring now to FIG. 1, the novel tongue depressor of the present invention is illustrated in the general direction of arrow 10 and can be seen to include a flat midsection 11 having curved opposite ends 12 and 13. The ends 12 and 13 are reverse curved and, as illustrated, the back end 12 is curved downwardly while the front or opposite end 13 is curved upwardly. The front end 13 is grasped by the fingers of the physician or surgeon, as illustrated in broken lines, and the major length of the depressor is inserted into the mouth with the underside of the depressor forcibly engaged with the tongue of the patient to urge the tongue down. The rearmost end of the depressor, identified by numeral 12, engages the base of the tongue and is used to slightly depress the tissues so that the observer can have a clear view of the throat region. To provide maximum viewing, end 12 is curved downward so that the terminating edge of end 12 does not interfere with observation.

Referring now in detail to FIG. 2, it can be seen that the tongue depressor 10 includes an elongated strip of material with the flat midsection 11 integrally connecting opposite curved ends 12 and 13. The opposite ends are reversed curved or curved in different directions. It is to be understood that the depressor may be composed of any suitable material such as plastic, wood veneer, flexible metal or the like. However, the composition of the material is to be of sufficient rigidity so that the physician or surgeon may manually depress the tongue and tissues in order to observe the throat area. If desired, the composition of the material may be transparent or translucent in order to provide greater observation of the throat area. The opposite curved ends 12 and 13 are rounded at the corners and on the sides, as represented by numeral 14, and further rounded at the terminating edges, as represented by numeral 15. Preferably, the rear end 12 is of sufficient width to fully depress the base of the tongue so that the glossal tissues will not obscure viewing of the throat area. Also, the width of the midsection 11 is somewhat reduced from the opposite ends 12 and 13 as the ends have lateral lobes or flares.

Referring now in detail to FIG. 3, it can be seen that the rearmost end 12 includes an underside which is concave as indicated by surface 16 while the top side, as indicated by numeral 17, is curved to follow the curvature of surface 16.

Referring now to FIG. 4, it can be seen that the front end of the depressor, indicated by numeral 13, is shaped with a reverse curvature from that shown in FIG. 3. Front end 13 includes a reverse concave curve surface 20 on the upper side of the depressor while the curvature 21 is a surface on the underside of the depressor. These curvatures with respect to front end 13 readily permit the user's fingers to grasp and firmly hold the depressor as it is maneuvered in the patient's mouth. Rear end 12 has a curvature which is compatible with the base of the tongue and greatly assists the physician or surgeon in viewing the throat areas.

Referring now in detail to FIG. 5, another embodiment of the invention is shown wherein the depressor is indicated in the general direction of arrow 30 having a midsection 31 with a shallow curve in elevational cross-sectional viewing and includes a front end 32 which is of a wider dimension than the width of the midsection 31. The rear end of the depressor includes an extension 32 which is folded or bent over upon itself or reverse directed at rounded connector 33 so as to reside in spaced relationship with respect to the underside of the midsection 31. The element 32 is of wider dimension than the width of the midsection 31 and is employed to depress the base of the patient's tongue. This embodiment is more particularly used in connection with an examination of the larynx with the physician employing a mirror. As the base of the tongue is depressed against the tissues, the element 32 may slightly become yieldable due to the shallow curve of the midsection so as to gently resist further depression of the tissues when resistance to the depression has increased.

FIG. 6 more clearly shows the greater width of the depression element 32 with respect to the width of the midsection 31 and the connector 33 of the depressor 30.

Referring now in detail to FIGS. 7 and 8, it can be seen that the tongue depressor may include a stick or other elongated member as illustrated by numeral 34 having an end insertably received into a receptacle 35 so that another embodiment of the invention is disclosed by numeral 36. The recess 35 is formed within a body 37 which terminates in a section or fold 38 so that a depression element 40 can be integrally carried on the body 37. The depression element 40 is in fixed spaced relationship with respect to the underside of the body 37. The embodiment 36 is used in the same manner as disclosed with respect to embodiment 30 shown in FIGS. 5 and 6. The recess or cavity 35 is open and is of sufficient depth to accept a portion of the stock or member 34 in an interference fit as it is inserted into the body 37. Thus, an elongated depressor is provided with a tissue depression element 40, as shown in FIG. 8.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A tongue depressor comprising:

an elongated body having a first end and a second end integrally connected together by a midsection;

said body having an upper surface extending between said first end and said second end across said midsection and an undersurface extending on an opposite side of said body between said first end and said second end;

said first end having a curved portion projecting away from said upper surface and terminating in a rounded edge;

said curved portion having side lobes laterally extending outwardly in spaced-apart relationship from said midsection;

said second end having a curved portion extending in an outwardly projecting direction from said undersurface;

said midsection is flexible between said first end and said second end;

said midsection has an arcuate cross section; and said second end includes said curved portion as a separate and individual part and includes an open-ended receptacle for insertably receiving said midsection in an interference type fit.

2. A tongue depressor comprising:

an elongated body having opposite ends separated by a midsection;

at least one end of said ends folded over upon itself in a reverse direction to reside in a straight edge immediately under said midsection in spaced-apart relationship;

said one integrally formed with said midsection and said midsection being arcuate in side elevational view;

lobes integrally carried on each side of said one end;

said midsection having a given width and said lobes laterally project beyond said given width of said midsection; and an end of said body opposite to said folded-over one end and terminating in a linear edge with a pair of opposite linear lateral flanges.

3. The tongue depressor defined in claim 2 wherein:

said body is composed of a flexible material and includes a shallow curve between said opposite ends.

4. The tongue depressor defined in claim 2 wherein:

said body is composed of a transparent material.

5. The tongue depressor defined in claim 2 wherein:

said midsection has an upper surface and an undersurface; and said folded-over one end defining an open cavity in cooperation with said undersurface.

6. A tongue depressor comprising:

an elongated flexible body having a first end and a second end integrally connected together by an arcuate midsection;

said body having an upper surface extending between said first end and said second end across said midsection and an undersurface extending on an opposite side of said body between said first end and said second end;

said first end having a curved portion folded over to reside in spaced-apart relationship with respect to said undersurface and terminating in a straight edge; and said curved portion having spaced-apart side lobes laterally extending from said curved portion.

7. The tongue depressor defined in claim 6 including:

said second end having a curved portion extending in an outwardly projecting direction from said undersurface.

* * * * *